United States Patent [19]

Hashimoto et al.

[11] 4,265,814
[45] May 5, 1981

[54] MATANSINOL 3-N-HEXADECANOATE

[75] Inventors: Naoto Hashimoto, Suita; Toyokazu Kishi, Nara, both of Japan

[73] Assignee: Takeda Chemical Industries, Osaka, Japan

[21] Appl. No.: 21,702

[22] Filed: Mar. 19, 1979

[30] Foreign Application Priority Data

Mar. 24, 1978 [JP] Japan .................................. 53-34644
Apr. 13, 1978 [JP] Japan .................................. 53-43946
Oct. 12, 1978 [JP] Japan ................................. 53-125989

[51] Int. Cl.³ ......................................... C07D 498/18
[52] U.S. Cl. ......................... 260/239.3 P; 424/248.54
[58] Field of Search ................................. 260/239.3 P

[56] References Cited

U.S. PATENT DOCUMENTS

| 4,137,230 | 1/1979 | Hashimoto et al. | 260/239.3 P |
| 4,151,042 | 4/1979 | Higashide et al. | 195/96 |
| 4,162,940 | 7/1979 | Higashide et al. | 435/119 |

OTHER PUBLICATIONS

Kupchan et al., "J. Med. Chem.", vol. 21, No. 1, pp. 31-37, (1978).

Primary Examiner—Robert T. Bond
Attorney, Agent, or Firm—Wegner & Bretschneider

[57] ABSTRACT

Maytansinoids of the formula:

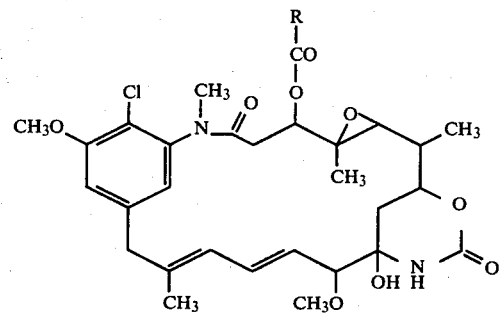

wherein R is hydrogen or alkyl of 1 to 15 carbon atoms are produced by contacting, in the presence of a carbodiimide, maytansinol with a carboxylic acid of the formula:

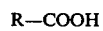

R—COOH wherein R has the same meaning as defined above.
In accordance with a second aspect of the invention there are provided novel maytansinoids of the formula

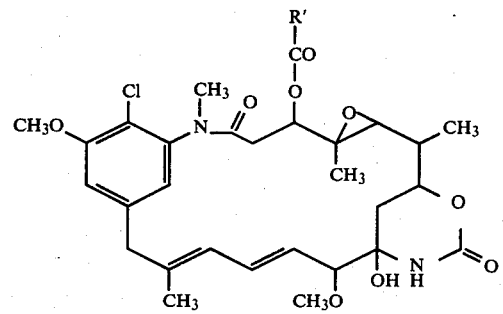

wherein R' is hydrogen, n-butyl or alkyl of 5 to 15 carbon atoms.

1 Claim, No Drawings

MATANSINOL 3-N-HEXADECANOATE

SUMMARY OF THE INVENTION

In a first aspect of the invention, there is provided a method of producing a maytansinoid of the formula:

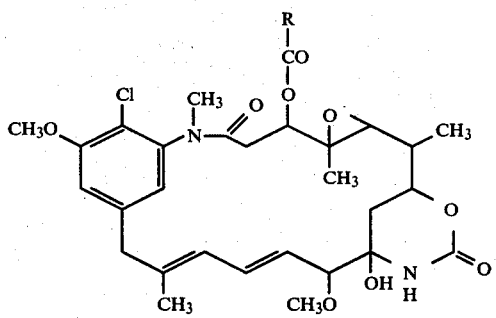

wherein R is hydrogen or alkyl of 1 to 15 carbon atoms, which comprises contacting, in the presence of a carbodiimide, maytansinol with a carboxylic acid of the formula:

R—COOH    (II)

wherein R has the same meaning as defined above.

Referring to the above formulas (I) and (II), the alkyl of 1 to 15 carbon atoms for R is a straight-chain or branched alkyl and exemplified by methyl (maytanacine, Antibiotic C-15003 P-1), ethyl (maytansinol propionate, Antibiotic C-15003 P-2), propyl (Ansamitocin P-3′, Antibiotic C-15003 P-3′), isopropyl (Ansamitocin P-3, Antibiotic C-15003 P-3), n-butyl, isobutyl (Ansamitocin P-4, Antibiotic C-15003 P-4), secondary butyl, tertiary butyl, n-pentyl, n-hexyl, n-heptyl, 3-heptyl, n-octyl, n-nonyl, n-decyl, n-undecyl, n-dodecyl, n-tridecyl or n-tetradecyl, n-pentadecyl and the like.

The maytansinoid of the above formula (I) includes novel compounds, i.e. those having hydrogen, n-butyl or alkyl of 5 to 15 carbon atoms.

Thus, in accordance with a second aspect of the invention there are provided novel maytansinoids of the formula:

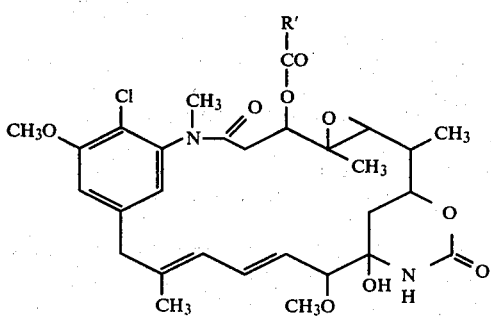

wherein R′ is a hydrogen, n-butyl or alkyl of 5 to 15 carbon atoms.

The maytansinoids (I) and (Ia) are useful as antimicrobial agents and also as antitumor agents.

DETAILED DESCRIPTION OF THE INVENTION

In the method of this invention, maytansinol is acylated with a carboxylic acid (II) in the presence of a carbodiimide.

With respect to maytansinol, use may be made of the carboxylic acid (II) in a proportion of about 1 to 500, preferably up to about 30 molar equivalents, and of the carbodiimide in a proportion of about 1 to 700, preferably up to about 50 molar equivalents.

The carbodiimide may be any compound having a carbodiimide linkage (—N=C=N—) which is convertible to a urea linkage (—NH—CO—NH—) during the contemplated acylation reaction. Thus, it may be, for example, a compound of the following formula:

$R^1$—N=C=N—$R^2$    (III)

wherein each of $R^1$ and $R^2$ is an organic radical which is capable of permitting the conversion of the carbodiimide portion to the corresponding urea during the reaction between maytansinol and the carboxylic acid (II). Accordingly, in the generic aspect of this invention, the actual nature of the substituents $R^1$ and $R^2$ is not of primary importance, with the limitation being present that the substituents permit the conversion of the carbodiimide group to a urea. Although particularly best results have been found using dicyclohexylcarbodiimide, $R^1$ and $R^2$ may also be independently selected from aliphatic and aromatic groups bearing further substituents that permit the conversion of the carbodiimide function to the corresponding urea. $R^1$ and $R^2$ may, for example, be independently of each other cycloalkyl which is unsubstituted or substituted with di-lower alkylamino, lower alkyl which is unsubstituted or substituted with di-lower alkylamino or morpholino, or phenyl which is unsubstituted or substituted with lower alkyl. Some examples of carbodiimides which may be preferably used are diphenylcarbodiimide, di-o-tolylcarbodiimide, di-p-tolylcarbodiimide, di-tert.-butylcarbodiimide, etc. as well as 1-cyclohexyl-3-(2-morpholinoethyl)carbodiimide, 1-cyclohexyl-3-(4-diethylaminocyanohexyl)carbodiimide, 1-ethyl-3-(2-diethylaminopropyl)carbodiimide, and 1-ethyl-3-(3-dimethylaminopropyl)-carbodiimide.

This reaction may be carried out in a suitable solvent such as esters, e.g. ethyl acetate; ethers, e.g. diethylether, dioxane, tetrahydrofuran, etc.; halogenated hydrocarbons, e.g. methylene chloride, chloroform, etc.; nitriles, e.g. acetonitrile; aromatic hydrocarbons, e.g. benzene; nitromethane; pyridine; dimethylformamide; dimethylsulfoxide; sulfolane; etc.; as well as a suitable mixture of such solvents.

This reaction may be conducted, for example, at a suitable temperature from ice-cooling up to refluxing temperature of the reaction system.

The acylation reaction proceeds more smoothly in the presence of a catalyst which is capable of enhancing the acylation of maytansinol. As examples of such catalysts there may be mentioned tertiary amines (e.g. aliphatic tertiary amines such as triethylamine; and aromatic tertiary amines such as pyridine, α-, β- or γ-picoline, 2,6-lutidine, 4-dimethylaminopyridine, 4-pyrrolidinopyridine, dimethylaniline, diethylaniline, etc.). In many cases, among those catalysts, 4-dimethylaminopyridine is most advantageous. The catalyst is employed in an amount sufficient to promote the acylation reaction. Thus, such suitable amount of the catalyst may in many cases be selected from the range of about 0.001 to 10, preferably, from about 0.01 to 1 molar equivalent to the carboxylic acid (II).

Where such a catalyst is employed, an amount of the carboxylic acid (II) may generally be reduced preferably to about 1 to about 6 molar equivalents to maytansinol.

The maytansinoid (I) produced in the above manner can be isolated and purified by routine procedures such as concentration, solvent extraction, chromatography, recrystallization, etc.

By the method of this invention thus far described, the maytansinoids (I) can be synthetically and advantageously produced.

Among maytansinods (I), those of the formula (Ia) are novel compounds. Particularly, compounds (Ia) having alkyl of 5 to 15 carbon atoms or R' are characterized by their lessened toxicity. As said alkyls, those of straight chain are desirable.

The maytansinoids (I) including the compounds (Ia) obtainable by the present method have useful antimitotic activity and antitumour activity. These activities, coupled with their low toxicity, make the compounds (I) useful for administration to tumour-bearing warm-blooded animals (e.g. mouse, rat, rabbit, dog, cat and human being) by oral and other routes to prolong their life spans. For the parenteral application of maytansinoid (I), it can be administered by the subcutaneous, intraperitoneal, intravenous, intramuscular or an other suitable route. The dosage may be chosen from the range of, for example, about 1 to 50 µg/kg body weight/dose, according to the condition of the disease, animal species and other factors.

Injectable solutions may be prepared, for example by dissolving about 50 µg to 3 mg of compound (I) in each about 0.5 ml of alcohol (e.g. methanol or ethanol) and adding thereto a sufficient amount of physiological saline to make 10 ml. When the dosage is small, this stock solution may be diluted with an additional amount of physiological saline.

The maytansinoids (I) according to this invention are useful also in that they display antimicrobial activities, e.g. antifungal activity and antiprotozoal activity. Thus, in employing compound (I) as an antifungal or antiprotozoal agent, it is useful for the assay of bacterial flora in samples of soil, active sludge and animal fluid. Thus, when useful bacteria are to be isolated from a soil sample or when the action of bacteria is to be assayed to the exclusion of the actions of protozoa and fungi for the operation and analysis of an active sludge system for effluent disposal, the maytansinoid (I) can be advantageously utilized for the purpose of ensuring a selective growth of bacteria without allowing the concomitant fungi and protozoa to grow and multiply. For such purposes, the test sample is added to a liquid or solid culture medium and, based on each 1 ml of the medium, 0.1 ml of a solution of about 10 to 100 µg/ml of compound (I) in 1% aqueous methanol is added, followed by incubation.

At level of application of 0.02 ml as a 1 mg/ml aqueous solution, maytansinoid (I) inhibits growth of pathogenic microorganisms such as the causative agents of the stem rot, Helminthosporium leaf spot and sheath blight of rice plants. Therefore, for the treatment of such plant diseases, the plants may be sprayed with a solution containing about 0.5 to 5 µg/ml of compound (I) in 1% aqueous methanol.

Maytansinol, which is used as the starting compound in the method of this invention, is known as a principle of plant life [Kupchan et al, J. Amer. Chem. Soc. 97, 5294 (1975)] and can also be produced by reductive cleavage of known maytansinoids.

Maytansinol can be advantageously produced also by the following procedure. Thus, an Antibiotic C-15003 producing microorganism belonging to the genus Nocardia (Deposit No.; FERM-P No. 3992, IFO-13726, ATCC-31281) is cultivated in a culture medium to accumulate the ansamitocin of the following formula (IV) in the culture broth.

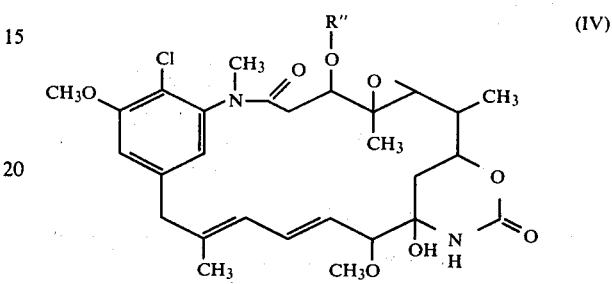

wherein R" is acetyl, propionyl, iso-butyryl, n-butyryl or iso-valeryl. This ansamitocin is then reductively hydrolyzed with a metal hydride compound such as LiAlH$_4$. [E. Higashide et al, Nature 270, 721 (1977); Offenlegungsschrift (West Germany) No. 27 46 209; and U.S. Pat. No. 4,137,230].

Incidentally, the maytansinoids (I) may be produced also by acylating maytansinol with use of a reactive derivative with respect to the carboxyl function of the carboxylic acid (II). As the reactive derivative for this purpose, there may be employed, for example, a carboxylic acid derivative having a functional group which is able to acylate the 3-position of maytansinol, such as an acid anhydride or acid halide (e.g. chloride, bromide, etc.) of (II). The solvent and catalyst which can be employed for this purpose are similar to those mentioned above in connection with the acylation reaction according to the method of this invention. The reaction temperature may be generally within the range of about 20° C. and 40° C. In case of an acid anhydride, the acylation may be promoted by conducting the reaction in the presence of the carbodiimide under similar conditions to those of the present method.

The method of this invention is superior to the just above-mentioned acylation reaction employing the reactive derivative of the carboxylic acid (II), especially in the yield of the object compound (I).

The following Examples and Reference Examples are intended merely to illustrate presently preferred embodiments of the present invention and not to restrict the scope of this invention.

Throughout the foregoing description as well as in the following Examples, Reference Examples and Claims, "g", "µl", "ml", "°C." and "N" respectively refer to "gram(s)", "microliter(s)", "milliliter(s)", "degrees centigrade" and "Normal(s)".

In the following Examples and Reference Examples, silica gel used for column-chromatography is the commercial product of Kieselgel 60, Art 7734 of E. Merck, West Germany unless otherwise referred to; melting points were determined on a Yanagimoto MP-S3 melting point apparatus (Yanagimoto Seisakusho, Kyoto, Japan), ultraviolet absorption spectra on a Hitachi ESP- 3T recording spectrophotometer, nuclear magnetic resonance spectra on a Varian EM-390 90 MHz NMR spectrometer and mass spectra on a JEOL JMS-01SC mass-spectrometer.

EXAMPLE 1

In 10 ml of methylene chloride were dissolved 100 mg (0.177 m mole) of maytansinol and 94 mg (1.068 m moles) of isobutyric acid, followed by addition of 225 mg (1.238 m moles) of dicyclohexylcarbodiimide (hereinafter briefly referred to as DCC) at about 22°-25° C. Following the addition of 43 mg (0.352 m mole) of 4-dimethylaminopyridine (hereinafter briefly referred to as DAMP), the mixture was stirred at that temperature for 5 hours, at the end of which time an additional 21 mg (0.172 m mole) of DAMP was added. The mixture was stirred at the same temperature for 18 hours. The resultant precipitate was separated by filtration and washed with methylene chloride. The filtrate and washings were combined, washed with water and dried. The solvent was distilled off under reduced pressure, then a small amount of ethyl acetate added to the residue and the mixture stirred and filtered to remove the insolubles. The filtrate was chromatographed on silica gel (75 g) with ethyl acetate saturated with water. The fractions giving an Rf value of about 0.31 on thin layer chromatography with the same solvent system were pooled, concentrated under reduced pressure and allowed to stand, the resultant crystals being collected by filtration. By the above procedure there was obtained 36.0 mg of compound (I) (R: isopropyl). The m.p., NMR, UV, mass spectra and thin layer chromatography data on the above product established it to be Ansamitocin P-3.

EXAMPLE 2

By a procedure similar to that described in Example 1, 100 mg of maytansinol (0.177 m mole) was reacted with 103 mg of isovaleric acid (1.010 m moles) and the crude reaction product was chromatographed. The fractions giving an Rf value of about 0.35 on thin layer chromatography (solvent: ethyl acetate saturated with water) were collected, concentrated under reduced pressure and allowed to stand. The resultant crystals were collected by filtration. By the above procedure there was obtained 27.5 mg of compound (I) (R: isobutyl). The m.p. NMR and thin layer chromatography data on this product established it to be Ansamitocin P-4.

EXAMPLE 3

To a solution of maytansinol (95.8 mg. 0.170 m mole) and n-decanoic acid (capric acid) (176.8 mg. 1.026 m moles) in dry dichloromethane (5 ml) was added DCC (245 mg, 1.189 m moles) and the mixture was stirred at room temperature for a short while until insolubles began to separate out. Then, following addition of DMAP (41.4 mg, 0.339 m mole), the mixture was stirred at that temperature for about 4.5 hours, after which a further amount (12.2 mg, 0.1 m mole) of DMAP was added. The mixture was stirred at room temperature overnight and the insolubles were filtered off. The filtrate was washed with 0.5 N-HCl (ca.10 ml) and saturated aqueous sodium hydrogen carbonate (ca. 10 ml) in that order and dried over anhydrous sodium sulfate. The solvent was distilled off and the residue was chromatographed on silica gel (75 g), elution being carried out with ethyl acetate. The eluate was collected in 16-g fractions, the fractions No. 12 through No. 40 were pooled and the solvent distilled off to recover 56.8 mg of crude product. This product was rechromatographed on a column of silica gel (25 g) and elution was carried out with chloroform (150 ml) and chloroform-methanol (40:1, v/v) (350 ml) in that order, the eluate being collected in 16-g fractions. The fractions No. 6 through No. 20 were pooled and the solvent was distilled off to recover a glassy solid. This glassy residue was dissolved in ethyl acetate and diethyl ether was added. By the above procedure there was obtained 42.6 mg of maytansinol 3-n-decanoate as a white sandy solid. m.p. 130°-134° C. (decomp.)

NMR spectrum (in CDCl$_3$) δ ppm: 0.83(3H, s), 0.85(3H, t, J=5.5 Hz), 1.05-1.85(17H, m), 2.2-2.7(4H, m), 2.87(1H, d, J=9 Hz), 3.16(3H, s), 3.18(1H, d, J=13 Hz), 3.37(3H, s), 3.48 (1H, d, J=9 Hz), 3.49(1H, d, J=13 Hz), 3.97(3H, s), 4.25(1H, m), 4.87(1H, dd, J=3 Hz & 12 Hz), 5.49(1H, dd, J=9 Hz & 15 Hz), 6.13(1H, d, J=11 Hz), 6.45(1H, dd, J=11 Hz & 15 Hz), 6.64(1H, s), 6.80(1H, d, J=1 Hz), 6.86 (1H, d, J=1 Hz).

UV spectrum (λmax, in MeOH) nm: 233, 240.5, 252.5, 281, 289.

MS spectrum (m/e): 657, 642, 625, 622, 615, 587.

EXAMPLE 4

The following compounds were obtained by procedures similar to that described in Example 3.

In the listing given below, the order of statements is as follows. The name of the product compound is followed by (1) the amount of maytansinol used (mg), (2) the carboxylic acid used and its amount (mg), (3) the amount of DCC used (mg), (4) the total amount of DMAP used (mg), (5) the yield of the product compound (mg), (6) the melting point of the product compound, (7) the NMR spectrum of the product compound (δppm, 90 MHz, in CDCl$_3$), with TMS as internal reference), (8) the UV spectrum of the same compound ($\lambda_{max}^{MeOH}$ nm) and (9) the mass spectrum of the same compound (m/e).

(A) Maytansinol 3-n-heptanoate
  (1) 102.1
  (2) Heptanoic acid, 141.4
  (3) 261.6
  (4) 67.3
  (5) 24.9
  (6) 158°-160° C. (decomp.)
  (7) 0.84 (3H, s), 0.88(3H, t, J=5.5 Hz), 1.1-1.8(11H, m), 2.14(1H, dd, J=3 Hz & 14 Hz), 2.2-2.54(3H, m), 2.50(1H, dd, J=12 Hz & 14 Hz), 2.87(1H, d, J=9 Hz), 3.15(3H, s), 3.17(1H, d, J=13 Hz), 3.37(3H, s), 3.46(1H, d, J=9 Hz), 3.49(1H, d, J=13 Hz), 3.99(3H, s), 4.25(1H, m), 4.87 (1H, dd, J=3 Hz & 12 Hz), 5.49(1H, dd, J=9 Hz & 15 Hz), 6.13(1H, d, J=11 Hz), 6.30(1H, s), 6.44(1H, dd, J=11 Hz & 15 Hz), 6.80(1H, d, J=1 Hz), 6.83(1H, d, J=1 Hz), etc.
  (8) 233, 240.5, 252.5, 281, 289
  (9) 676, 659, 633, 615, 600, 583, 580, 573, 545

(B) Maytansinol 3-n-tridecanoate
  (1) 97.5
  (2) Tridecanoic acid, 219.3
  (3) 246.3
  (4) 44.3
  (5) 39.5
  (6) 110°-116° C. (decomp.)
  (7) 0.83(3H, s), 0.85(3H, t, J=5.5 Hz), 1.05-1.85(23H, m), 2.2-2.7(4H, m), 2.87(1H, d, J=9Hz), 3.16(3H, s), 3.18(1H, d, J=13 Hz), 3.37(3H, s), 3.48(1H, d, J=9 Hz), 3.49(1H, d, J=13 Hz), 3.97(3H, s), 4.25(1H, m), 4.87(1H, dd, J=3 Hz & 12 Hz), 5.48(1H, dd, J=9 Hz & 15 Hz), 6.12(1H, d, J=11 Hz), 6.44(1H, dd, J=11 Hz & 15 Hz), 6.55(1H, s), 6.30(1H, d, J=1 Hz), 6.86(1H, d, J=1 Hz), etc.

(8) 233, 240.5, 253, 282, 289.5

(9) 699, 684, 667, 664, 657, 629.

EXAMPLE 5

In 5 ml of dry dichloromethane was dissolved 101.3 mg of maytansinol, followed by the addition of n-hexadecanoic acid (palmitic acid) (260.3 mg, 1.015 m moles), N-cyclohexyl-N'-(3-diethylamino)propylcarbodiimide.hydrochloride (224.8 mg, 0.911 m mole) and DMAP (43.6 mg, 0.357 m mole). The mixture was stirred at room temperature for 3 hours, at the end of which time a further amount (20.9 mg, 0.171 m mole) of DMAP was added. The mixture was stirred at room temperature overnight. A still additional amount (44 mg, 0.361 m mole) of DMAP was further added, followed by stirring at room temperature again overnight. The reaction mixture was then chromatographed on a column of silica gel (75 g) with ethyl acetate, the eluate being collected in 16-g fractions. The fractions No. 9 through No. 20 were pooled and the solvent was distilled off. The crude product thus obtained was rechromatographed under the same conditions as above, the fractions No. 11 through No. 20 were pooled and the solvent was distilled off to recover 38.3 mg of residue. This was recrystallized from diethyl ether-hexane to obtain 24.0 mg of maytansinol 3-n-hexadecanoate as white powders.

m.p. 105°-116° C. (decomp.).

NMR spectrum (in CDCl$_3$) δ ppm: 0.83(3H, s), 0.85(3H, t, J=5.5 Hz), 1.0-1.85(29H, m), 1.70(3H, s), 2.2-2.7 (4H, m), 2.87(1H, d, J=9 Hz), 3.16(3H, s), 3.18(1H, d, J=13 Hz), 3.37(3H, s), 3.47(1H, d, J=13 Hz), 3.97 (3H, s), 4.25(1H, m), 4.87(1H, d, J=3 Hz & 12 Hz), 5.49(1H, d, J=9 Hz & 15 Hz), 6.12(1H, d, J=11 Hz), 6.45 (1H, dd, J=11 Hz & 15 Hz), 6.80(1H, d, J=1Hz), 6.85(1H, d, J=1 Hz), etc.

UV spectrum ($\lambda_{max}^{MeOH}$ nm: 233, 240(sh), 252.5, 281, 289.5.

MS spectrum (m/e): 741, 726, 706, 699.

EXAMPLE 6

To a solution of maytansinol (107.1 mg, 0.1895 m mole) and DCC (195.2 mg, 0.9476 m mole) in 5 ml of dry dichloromethane, were added 26 μl (0.69 m mole) of 99% formic acid and 46.2 mg (0.3787 m mole) of DMAP. After two hours' stirring, DCC (195.6 mg, 0.9495 m mole), formic acid (99%; 26 μl, 0.69 m mole) and DMAP (47.0 mg, 0.3852 m mole) were further added and the mixture was stirred overnight at room temperature. The insolubles were filtered off and the filtrate was evaporated to dryness. The residue was subjected to preparative thin layer chromatography on precoated silica gel plates (Art 5717, Merck) developed twice with ethyl acetate saturated with water to give 12.2 mg of maytansinol 3-formate as a glassy substance. Rf-value on a thin layer chromatography on Merck precoated silica gel plate (HPTLC, Art 5642, E. Merck) with ethyl acetate saturated with water as solvent: 0.54 (cf., Rf-value of maytansinol under the same conditions: 0.35).

EXAMPLE 7

To a solution of maytansinol (103.7 mg, 0.1835 m mole) and n-valeric acid (113 mg, 1.108 m moles) in dichloromethane (10 ml) was added DCC(265 mg, 1.286 m moles) and the mixture was stirred at room temperature for a short while. Then, following addition of DMAP(45 mg, 0.369 m mole), the mixture was stirred at that temperature for 3 hours, after which a further amount (23 mg, 0.189 m mole) of DMAP was added and the mixture was stirred at room temperature for 15 hours. The insolubles were filtered off and the filtrate was concentrated under reduced pressure. The residue was admixed with about 5 ml of ethyl acetate to remove the insolubles by filtration. The filtrate was concentrated under reduced pressure and the residue was purified by three successive chromatography on silica gel (1) SiO$_2$ (75 g) with ethylacetate, (2) SiO$_2$(35 g) with chloroform-methanol (40:1, v/v) and (3) SiO$_2$(75 g) ethyl acetate in that order. The fractions giving a spot of Rf value of about 0.34 on thin layer chromatography with ethyl acetate saturated with water were pooled, concentrated under reduced pressure. To the residue dissolved in ethyl acetate was added diethyl ether to give precipitates which were harvested by filtration. By the above procedure there was obtained 35 mg of maytansinol 3-n-pentanoate as crystals.

m.p. 165°-168° C.

NMR spectrum (in CDCl$_3$) δ ppm: 0.83(3H, s, 4-C$\underline{H}_3$), 0.96 (3H, t, J=6 Hz; —COCH$_2$CH$_2$CH$_2$C$\underline{H}_3$), 4.87 (1H, dd, J=3 Hz & 12 Hz; 3-$\underline{H}$), 6.83(2H, substantially singlet; aromatic H)

EXAMPLE 8

In a manner similar to those of the preceding Examples, there are obtained the following compounds:

(C) Maytansinol 3-n-hexanoate m.p. 159°-162° C. (decomp.).

NMR spectrum (in CDCl$_3$) δ ppm: 0.83(3H, s), 0.87(3H, t, J=6 Hz), 1.05-1.8(9H, m), 1.69(3H, s), 2.2-2.54(4H, m), 2.87(1H, d, J=9 Hz), 3.16(3H, s), 3.22(1H, d, J=13 Hz), 3.37(3H, s), 3.46(1H, d, J=9 Hz), 3.49(1H, d, J=13 Hz), 3.97(3H, s), 4.21(1H, m), 4,87(1H, dd, J=3 Hz & 12 Hz), 5.49(1H, dd, J=9 Hz & 15 Hz), 6.12(1H, d, J=11 Hz), 6.44(1H, dd, J=11 Hz & 15 Hz), 6.79(1H, d, J=1 Hz), 6.81(1H, s), 6.82(1H, d, J=1 Hz), etc.

UV spectrum (in MeOH, λmax) nm: 233.5, 241, 252.5, 281, 289.

MS spectrum (m/e): 615, 601, 586, 569, 566, 559, 531.

(D) Maytansinol 3-n-octanoate m.p. 151°-160° C. (decomp.).

NMR spectrum (in CDCl$_3$) δ ppm: 0.83(3H, s), 0.87(3H, t, J=5.5 Hz), 1.1-1.8(13H, m), 1.68(3H, s), 2.2-2.7 (4H, m), 2.86(1H, d, J=9 Hz), 3.15(3H, s), 3.19(1H, d, J=13 Hz), 3.37(3H, s), 3.40(1H, broad), 3.48(1H, d, J=9 Hz), 3.50(1H, d, J=13 Hz), 3.97(3H, s), 4.24(1H, m), 4.85(1H, dd, J=3 Hz & 12 Hz), 5.48(1H, dd, J=9 Hz & 15 Hz), 6.11(1H, d, J=11 Hz), 6.43(1H, dd, J=11 Hz & 15 Hz), 6.77(1H, d, J=1 Hz), 6.80(1H, s), 6.83(1H, d, J=1 Hz).

UV spectrum (in MeOH, λmax) nm: 233.5, 241, 252.5, 281, 289.

MS spectrum (m/e): 629, 614, 597, 594, 587, 559.

REFERENCE EXAMPLE 1

To a mixed solution of 108.1 mg maytansinol and 302 mg isobutyric anhydride in 5 ml of dichloromethane was added 47.1 mg of DMAP at room temperature. The mixture was stirred at that temperature for 100 minutes, at the end of which time a further 24.2 mg of DMAP was added. The entire mixture was stirred at room temperature overnight. Next morning, the reaction mixture was shaken with 10 ml of 0.5 N-HCl and the dichloromethane layer was taken and dried (over Na$_2$SO$_4$). The solvent was distilled off and the residue was chromatographed on silica gel (75 g) (solvent: ethyl acetate: ethyl acetate saturated with water=2:1(v/v).) The eluate was collected in 16-g fractions and the fractions No. 17 through No. 30 were pooled and concentrated under reduced pressure. The residue was dissolved in 5 ml of chloroform, washed with 10% aqueous sodium hydrogen carbonate and water in that order and dried (over Na$_2$SO$_4$). The solvent was distilled off under reduced pressure, the residue dissolved in a small amount of acetic acid, allowed to stand and the resultant crystals recovered by filtration. By the above procedure there was obtained 35.5 mg of compound (I) [R: isopropyl] m.p. 190°-192° C. The elemental analysis, mass spectrum, IR spectrum, UV spectrum and thin layer chromatogram (Rf) of this product were in agreement with those of Ansamitocin P-3.

REFERENCE EXAMPLE 2

In a mixture of 1 ml triethylamine and 50 ml of dimethylformamide was dissolved 100 mg of maytansinol and, while the solution was stirred under ice-cooling, 50 μl of isobutyryl chloride was added dropwise. The mixture was stirred under ice-cooling for 30 minutes and then, at room temperature for 2.5 hours, after which it was distilled under reduced pressure. The residue was dissolved in 10 ml of dichloromethane, washed with water and dried (Na$_2$SO$_4$). The solvent was distilled off under reduced pressure and the residue was chromatographed and recrystallized as in Reference Example 1. By the above procedure there was obtained 19.4 mg of Ansamitocin P-3.

REFERENCE EXAMPLE 3

In 1.0 ml of dichloromethane was dissolved 23.5 mg of maytansinol and, at 22° C., 70.5 mg(ca. 10 mol. equiv.) of acetic-formic anhydride (prepared by cooling 2 ml of acetic anhydride to −5° C.-0° C., adding 1 ml of 99% formic acid at that temperature over about 10 minutes, heating the mixture to 50° C. for 15 minutes and cooling it rapidly to 0° C.), as well as 11.7 mg of DMAP, was added. The mixture was stirred at room temperature (ca. 22° C.) overnight. Then, 10 drops of methanol were added to this reaction mixture, followed by stirring at room temperature for 3 hours. The mixture was concentrated to dryness under reduced pressure, the residue was applied to a silica gel preparative thin layer chromatoplate, and was developed twice with water-saturated ethyl acetate. The zone near 6.0 to 8.0 cm above the origin was scraped of the plate and extracted with 10% methanol-dichloromethane. the solvent was then distilled off under reduced pressure. By the above procedure there was obtained 8.35 mg of maytansinol 3-formate as a colorless glassy substance.

NMR spectrum (in CDCl$_3$) δ ppm: among others, 0.85 (3H, s; 4-C$\underline{H}_3$), 4.83(1H, dd, J=3 Hz & 11 Hz; 3-$\underline{H}$), 8.01(1H, s; 3-OC$\underline{H}$O)

REFERENCE EXAMPLE 4

To a solution of maytansinol (102.7 mg) in dichloromethane (10 ml) there were added caproic anhydride (145.7 mg), DCC (207 mg) and DMAP (46.5 mg), and the mixture was stirred at room temperature for 5 hours. The reaction mixture was chromatographed on silica gel with ethyl acetate to obtain 56.5 mg of maytansinol 3-n-octanoate.

What is claimed is:

1. A maytansinoid of the formula:

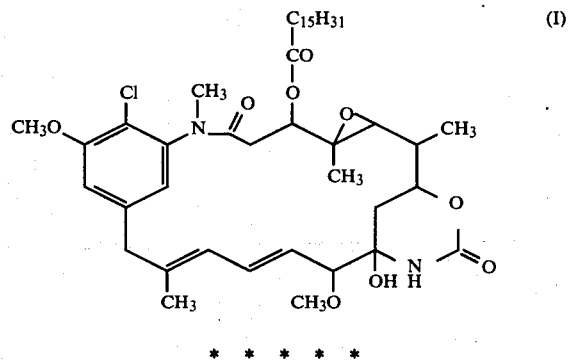

* * * * *